United States Patent [19]

Dooley

[11] Patent Number: 4,577,487

[45] Date of Patent: Mar. 25, 1986

[54] PRESSURE VESSEL TESTING

[76] Inventor: John G. Dooley, 5282 Pastatiemop Dr., Yorba Linda, Calif. 92686

[21] Appl. No.: 681,605

[22] Filed: Dec. 14, 1984

[51] Int. Cl.[4] .................. G01N 29/04; G01M 3/24
[52] U.S. Cl. ................................. 73/37; 73/587
[58] Field of Search ........................ 73/587, 37

[56] References Cited

U.S. PATENT DOCUMENTS

| 3,545,262 | 12/1970 | Steele et al. | 73/37 |
| 3,926,036 | 12/1975 | Bower | 73/37 |
| 4,002,054 | 1/1977 | Grenci | 73/37 |
| 4,039,376 | 8/1977 | Wachter | 73/587 |
| 4,468,965 | 9/1984 | Blackburn | 73/587 |
| 4,481,818 | 11/1984 | Hellqvist | 73/587 |

FOREIGN PATENT DOCUMENTS

| 2937709 | 4/1981 | Fed. Rep. of Germany | 73/587 |
| 89745 | 7/1980 | Japan | 73/587 |
| 7914 | of 1894 | United Kingdom | 73/37 |

Primary Examiner—Stewart J. Levy
Assistant Examiner—Joseph W. Roskos
Attorney, Agent, or Firm—Grover A. Frater

[57] ABSTRACT

Pressure vessels are tested for structural integrity by recording acoustic events generated in the vessel's walls while it is immersed in water and subjected to internal pressure above the vessel's working pressure. Acoustic events are recorded by sensors fixed either to the wall of the vessel or to the walls of the water container in which the test is conducted. In preferred form, the vessel is water filled throughout the test and its volumetric increase with pressure is measured in an initial over-pressurization.

19 Claims, 4 Drawing Figures

PRESSURE VESSEL TESTING

TECHNICAL FIELD

This invention relates to a testing of pressure vessels for structural integrity.

BACKGROUND ART

Standards for evaluating the structural integrity of vessels whose contents are to be stored under pressure are adopted by the American Society of Mechanical Engineers, the American Society for Testing of Materials, and other professional and industrial organizations. Certain governmental agencies adopt and enforce such standards. One of those agencies is the United States Department of Transportation which has promulgated test procedures to be employed in testing cylinder used in transporting pressurized gasses. Those procedures are set out in the Department's "Hazardous Material Regulations" in 49 CFR, subpart B, 107 et seq. The regulations include a requirement that certain classes of cylinders by hydrostatically retested periodically. Cylinders are immersed in a water tank and are pressurized to a value above service pressure. The vessel's volumetric increase incident to pressure increase is measured, and structural integrity is assumed if the vessel has not ruptured and if volumetric increase has not exceeded a predefined proportion of its unpressurized volume.

The Department of Transportation tests determine the likelihood of eminent rupture and any reduction in wall thickness resulting from corrosion. The number of pressure vessel failures is very small, which suggests that the procedure is basically sound from a safety standpoint. On the other hand, the good safety record may indicate that safety margins in vessel design are more than adequate. The combination of better test methods and narrower safety margins may result in cost saving both in the initial production and in the handling and transportation of vessels, and in increased safety. A substantial amount of effort is being devoted to the development of improved testing methods and apparatus in the search for greater safety at lower cost.

The kind of fault that is not detected in the hydrostatic pressure testing is the growth of microscopic cracks that can, and do, become large cracks and eventually rupture points.

The formation of microscopic cracks in metals, including pressure vessel steels, is the mechanism by which internal stresses developed in the material in the material making or vessel fabrication processes are relieved. Subsequent stressing of the material, as by subjecting a vessel to internal pressure, causes relative movement of the material about the crack, and that movement generates acoustic events which can be detected using microphones. The frequencies of those events are in the ultrasonic range in general, and the microphones are called acoustic transducers. They rely on piezoelectric phenomenon, are very sensitive to a wide range of frequencies. They are high impedance devices which gives rise to considerable difficulty in practice.

Large scale users of pressure vessels subject to Department of Transportation test requirements, interested in minimizing the cost of periodic testing, have done a substantial amount of work in an effort to develop tests that can be conducted without immersion in water and without removing the vessels from their carriers. Acoustic events are initiate by pneumatic pressurization in open air and are detected. Interpretation of results is made very difficult because, in that environment, the signal to noise ratio is low. In practice, supplimentary non-destructive testing using penetrating dyes, magnetic flux and ultrasonic thickness measurements and the like are required. It is necessary to use multiple piezoelectric transducers and to measure differences in signal arrival times whereby to permit mapping of cracks. Acoustic events occur as bursts of acoustic energy, and are rich in harmonics. The result is a mass of acoustic data including phase differences in primary data, reflections, many frequencies, and noise both mechanical and electrical in a wide range of frequencies and energy levels.

To cope with that situation, it has been necessary to establish threshholds of amplitude, signal rise time, interval between events and the like, above which further inspection is assumed to be required and below which the test is assumed to have been passed. The threshholds are established at some value above worst condition ambient noise, which means above the aggregate of the acoustic value of conversion, air movement, temperature induced dimensional change, and vibrations caused by movement of people and things in the vicinity of the test. In the last analysis, the threshold is set at some arbitrary value which seems to permit accurate mapping of event origins.

The sensitivity of acoustic sensors is entirely adequate, and the use of preamplifiers as impedance changers greatly reduces the problems of electrical noise in processing of acoustic event signals. What is required, and what it is a purpose of this invention to provide, is test apparatus and techniques that permit better recognition of acoustic events that are the precursors of vessel failure.

DISCLOSURE OF INVENTION

It is an object of this invention to provide an improved method and apparatus for testing the structural integrity of pressure vessels.

Another object is to provide a method which involves examination of acoustic events incident to pressurization of a vessel in a way that minimizes problems associated with ambient noise.

Another object is to provide improved methods and apparatus with which to map the location of acoustic events.

These and other objects and advantages of the invention are realized, in part, by the provision of a test jacket in which acoustic events incident to pressurization of a vessel can be measured while the vessel is immersed in water. and, in preferred form, is filled with water. Sensors located at fixed points on the jacket wall make a record of ambient noises specific to the facility for subtraction or deletion from test data gathered by those sensors. Such sensors permit rotation of the vessel to facilitate the mapping of the sites of recurring acoustic events. Similar provision is made for subtraction or deletion of ambient noise measured before pressurization from test data taken during pressurization where the data is taken with sensors fixed to the vessel. Sensors fixed to the test jacket are preferred but in some applications both sensor arrangements are employed.

Acoustic event measurement has the advantage that it reveals the position in the vessel wall of the source of energy release. The location being known, further non-destructive testing with penetrating dye, magnetic flux, and sonic reflection mapping and the like, can be conducted in an effort to assess whether there is a danger to vessel integrity. In one preferred method sonic reflection mapping is employed.

A problem in acoustic event detection is that the amplitude of events of interest is very often no greater than, or is less than, noise amplitude.

The acoustic events of interest are the consequence of slippage of the material of the vessel wall relative to adjacent material. The mechanism of that slippage is complex and not well understood. Slippage at grain boundaries does not necessarily indicate separation. The forces that bind adjacent grains in steel appear to continue to operate in most instances despite slippage resulting from stress. Reversal appears to occur over a period of time after stress is reduced. Reversible slippage appears to be a normal incident to shape distortion below the yield point in alloyed material.

The formation of microscopic internal cracks occurs at grain boundaries as an incident to relieving strains built into the material of the vessel wall during manufacture and as a result of initial stressing of the material. Movement occurring between the side walls of those cracks may account for acoustic events during vessel pressurization and depressurization, but those sounds do not foretell vessel failure.

It is growth of cracks that is of concern. It is the crack that increases in size under pressurization that may eventually result in rupture. It is known that such cracking occurs as a sequence of material separations each of which may be very limited. The process can be likened to what occurs as a broom handle cracks and breaks as steadily increasing bending force is applied. Initial cracking ordinarily does not result in complete breakage. Instead, further cracking usually does not occur until there is an increase in bending force. Each increase beyond the magnitude of previous force results in further cracking.

There are other causes of noise generation. Overpressurizing may cause chips of scale and paint to break loose, fasteners to creep, and leaking at the vessel opening, not apparent at service pressures. External vibrations that reach the sensors and electrical noise in the signal processing equipment add apparent acoustic events.

To the extent that this understanding of the several causes of acoustic events generation during vessel pressurization is correct, the task of evaluating vessel integrity on the basis of acoustic signals involves identification of those acoustic events which result from crack growth.

If the environment is maintained constant, ambient noise such, for example, as the sound of vessel pressurizing pumps if they must be operated while data is taken, can be deleted from test data. To do that is one of the features of the invention. The test is conducted in a water test jacket which is insulated from mechanical vibrations. Fortunately earth is an excellent sound deadening material, so it is convenient to install the water jacket in which the tests will be conducted in a bore in the earth. The hangers by which vessels are held suspended in the vessel are connected to the vessel are arranged to offer high impedance to acoustic transmissions. So, too, are vessel pressurization lines. One of the major advantages in conducting tests while the vessel is immersed in water, rather than in air, is that water offers very much greater impedance to acoustic transmission than does air. Conversation, winds, and other ambient noises generated in the surrounding air, are not heard underwater.

The higher impedance of water makes it preferable to gas as the pressurizing medium. One of the tasks in testing for acoustic events is to map the source of events of interest. One form of mapping involves detecting the time difference between arrival of sound at each of two or more sensors. For example, if the sound of an event reaches two spaced sensors at the same time, it can be assumed, if the transmission medium to the two sensors is the same, that the event occurred midway between the sensors. If, instead, sound to one arrives before it arrives at the other, the event is assumed to have occurred at a point closer to the sensor which received the signal first. The lower sound velocity in water results in greater arrival time differentials and greater signal resolution. Another form of mapping makes use of the fact that sound is attenuated greatly by water. The source of an acoustic event can be found by comparison of the amplitude of acoustic energy arriving at spaced sensors.

Whichever method is used, the vessel under test is filled with water as well as being immersed in it. The effect is to damp ringing inside the vessel and without. Reverberation being minimized, acoustic events initiate what is readily detected as a burst of acoustic energy from the same source notwithstanding that is is detected at different times and with different amplitude. The wave form of the signal identifies its source as an acoustic event. Amplitude and arrival time difference define the source position. But there is still another important factor which can be and is used in the invention. Discontinuities in the walls of the vessel under test reflect ultrasound and can be detected by measuring the relative amplitude and the difference in arrival times of reflections of ultrasound signals directed toward the vessel under test. Some pressure vessels are fourty feet long and just under ten inches in diameter. In the case of such vessels it is preferred to rely on signal wave shape to identify flaws that grow and to rely primarily on amplitude difference measurement to map approximate fault location. Greater resolution of fault location is achieved by the reflection measuring method.

Position mapping is highly developed in the acoustic typewriter art, seismic exploration and others. It is accomplished in the invention by a microprocessor which is part of the signal processing equipment using input from as many as two sets of eight or more spaced sensors.

The invention may be practiced using sensors attached to the vessel walls or with sensors fixed to the walls of the test jacket. Both arrangements have advantages, and there is also advantage in employing both. Acoustic wave propagation is high in metal. Sensors fixed to the vessel will detect even very low amplitude acoustic events. On the other hand, sensors fixed to the jacket walls detect certain kinds of input noise with the same resolution and amplitude in each test. Cancellation of that kind of noise is accomplished more accurately when the sensors are not moved from test to test. As indicated above, transmission velocity is lower through water than through the metal of the vessel whereby the interval between the times when acoustic events are detected in spaced sensors is longer and mapping can be more accurate. Also, if a growing crack is indicated by a continuing sequence of events, the vessel can be rotated in the test jacket relative to the fixed sensors to verify mapping of those events. In addition, in the preferred method and apparatus, mapping is accomplished, or verified in the case of long vessels, by measuring amplitude and arrival times of reflections from vessel faults of sonic emissions from sounders fixed to the test jacket wall. Furthermore, if two sets of sensors are employed, one on the vessel and another on the jacket wall, comparison of their output, after adjustment for transit time through the water of ambient noise and acoustic events, will permit easier identification of the acoustic events.

The fact that several alternative arrangements are possible is due in large measure to the advantages of the water test environment. Fewer, more closely spaced sensors simplify locating acoustic events in the testing of small gas cylinders so the complexity of fault mapping by listening to reflections and acoustic events need not be tolerated.

DESCRIPTION OF THE PREFERRED EMBODIMENT

Figure 2:
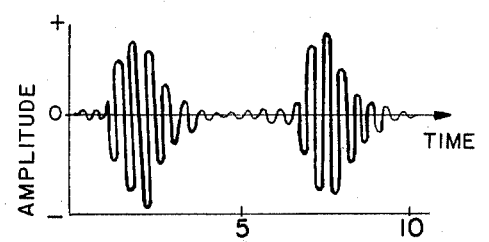
FIG. 2 is a graph of one form of the electrical signal variations with time that are generated in the acoustic sensors in response to crack growth.
Figure 3:
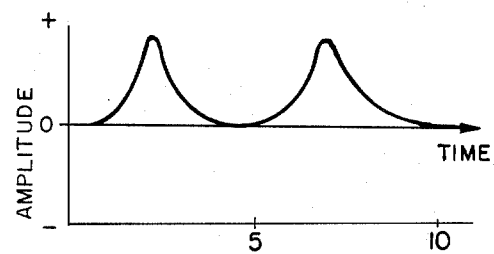
FIG. 3 is a graph of the signals of FIG. 2 after integration.

Typical acoustic events are graphed in FIG. 2. The ordinate represents amplitude. The abscissa represents time. The higher frequency components of these wave forms may fall in the range 100 kHz to 200 kHz and are higher in frequency than most noise. However, that they are acoustic events generated in the metal wall of a vessel is indicated less by their frequency and amplitude than by their wave shape and, in particular, by the low frequency components in the rise and fall of event vibrations. Those components can be seen in the integration of the rectified form of event signals. The result of integration is shown in FIG. 3. Here, the waves are characterized by relatively fast rise time and slow decay. The lower frequency components of the FIG. 2 representation fall in the range of much of the ambient noise that is encountered in practice. Accordingly, one way to evaluate an acoustic event test system and method is to examine its ability to find the lower frequency components of acoustic events and its ability to exclude low frequency noise from the sensors. Fortunately, conducting the tests in a reasonably isolated water environment results in attenuation of ringing and exclusion of much of the noise, and testing in water (or other liquid) is one of the salient features of the invention.

Special processing is sufficiently advanced to permit the extraction of large amounts of information from basic data. The water environment provides clearer acoustic event signals at improved signal to noise ratios. It remains only to arrange the test procedure so that the requisite information is contained in the test data.

As in the case of the broom handle, the generation of an acoustic event from a growth fault requires that the vessel be subjected to a pressure higher than the previous event producing level. That will be some pressure above service pressure but not necessarily as high as the maximum expansion test pressure. The preferred method is to increase pressure in several steps increasing the level at each step until the prescribed level of the Department of Transportation hydrostatic pressure test is reached. Volumetric change at that pressure is measured and recorded. Any acoustic events that occur in the process are recorded and mapped. In that process the occurrence of more than one event at any location will be detected. The pressure at which events occur is also recorded. That having been done, the hydrostatic test has established whether the elasticity of the vessel material is within safe limits and a record of acoustic event activity is available for assessing the probability that the vessel wall is safe or unsafe. The absence of acoustic events can be interpreted to mean that the vessel is safe and retesting can reasonably be postponed for a longer time than is reasonable when only the hydrostatic pressure test result is known. On the other hand, if a series of acoustic events were initiated beginning at low test pressure levels, further non-destructive testing to discover the size and exact position of the fault is indicated. The evaluation of the vessel's serviceability would be based on the finding in these additional tests. In the intermediate case in which acoustic events occur only at the higher test levels, vessels which pass the hydrostatic pressure test would be marked for retesting at an earlier time.

The test is conducted with the vessel completely filled with water, and completely immersed in water. Water is preferred because of its availability and low cost. In preferred testing the vessel is suspended from its neck at one end. Pressure is raised to 100 percent of test pressure, which might be five thirds of rated service pressure, in no less than two and preferably four steps. Holding pressure constant at each level for thirty seconds is adequate unless more time is required for signal processing. To provide the maximum difference in test conditions, it is preferred that the several test pressure levels differ by the same percentage of maximum increase over service pressure. But, if there are only two levels it is preferred that first be at about 90 percent of final test pressure.

Figure 4:
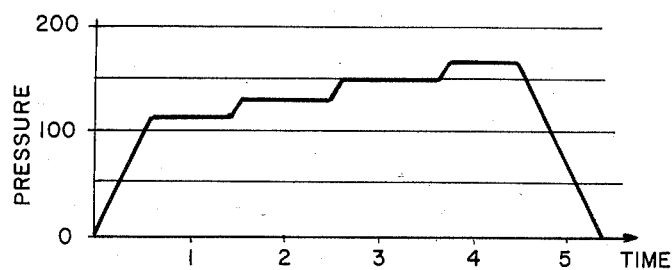
FIG. 4 is a graph of the variation in vessel pressurization with time in the preferred test method.

In the preferred arrangement the acoustic signals are integrated and filtered to extract components in the range 5 kHz to 50 kHz. The analog information is converted to digital information and that information is recorded. FIG. 4 illustrates a preferred pressurization sequence.

The signals from the several sensors are processed separately to identify the acoustic signals whose general form corresponds to the forms shown in FIGS. 2 and 3, and other forms which empirical data suggests is useful in predicting failure. Those signals having been identified in the output of the several sensors, they are compared in time and amplitude to fix their point of origin in the vessel wall.

Figure 1:
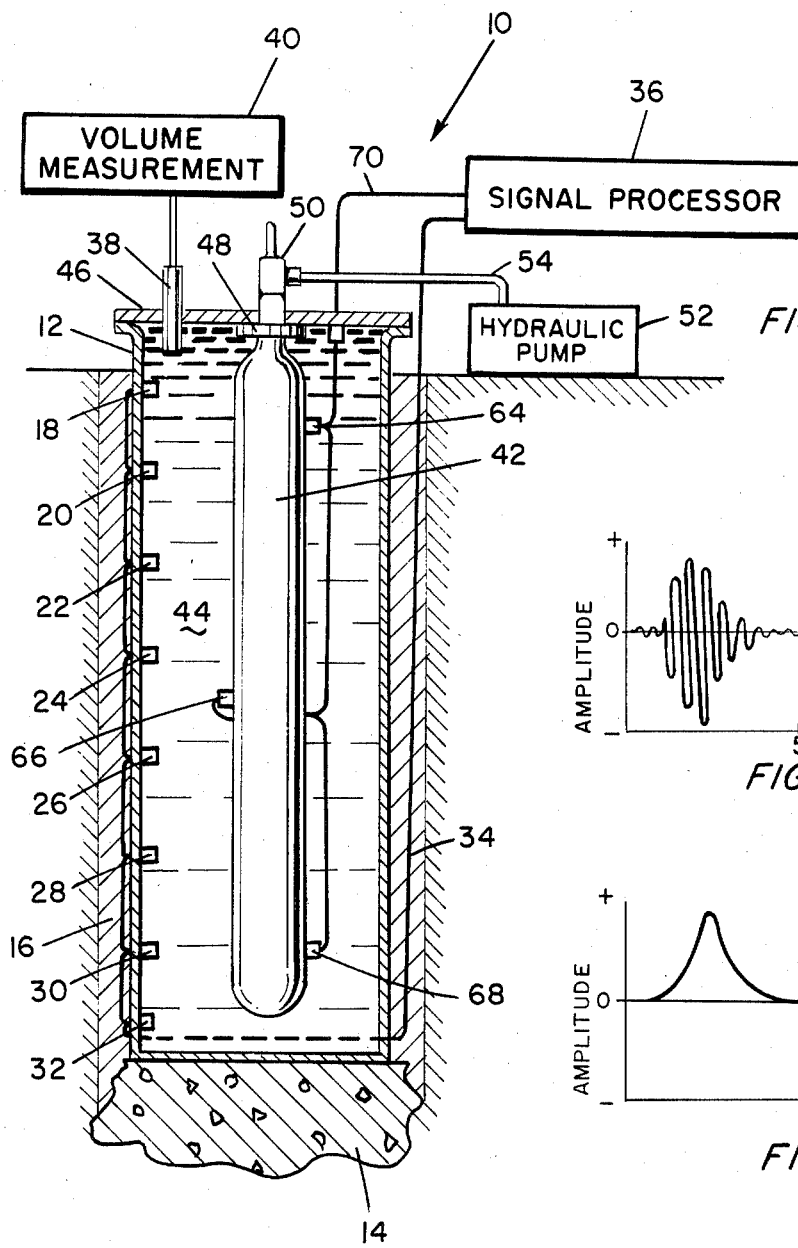
FIG. 1 is a schematic diagram of a test apparatus according to the invention.

The test apparatus 10 of FIG. 1 includes a cylindrical water test jacket 12 which is installed lengthwise in the earth such that its open upper end is at ground level. Its dimensions are determined by the size of vessels to be tested. Two standard sizes for high pressure vessels are used to transport materials over the highways. One is nine and five-eights inches in diameter and twenty-one feet long. The other is twenty-two inches in diameter and thirty-four feet long. However, forty foot long vessels are not uncommon. It is possible to test at least two such vessels with a single set of sensors so a suitable jacket dimension for testing such vessels would have an inner diameter of about 28 inches and would be about 42 feet long. That diameter permits suspending two such vessels with about three inches clearance between vessels and three inches clearance between the vessels and the jacket wall. Welded steel, protected against rusting, is the preferred material. An attempt is made to insulate the jacket against external sounds.

The jacket is supported on a concrete block 14 to insure against displacement in the vertical direction, but the excavation around the jacket is filled with a sound insulating material. One of the best and least expensive for use in the earth is a light soil screened to remove stones and debris. Soils are poor conductors of sound, and the insulating layer 16 in FIG. 1 is a light loam.

A number of piezoelectric acoustic event sensors are fixed on the wall of the jacket such that they are coupled directly to the water. Eight of them, numbered 18, 20, 22, 24, 26, 28, 30 and 32, respectively, are visible in FIG. 1. Each sensor includes a preamplfier whose purpose is to amplify signals and to match the sensor to the impedance of the cable 34 by which sensor output is applied to the signal processor 36. Apparatus is included for measuring the increase in water level in the tank during the over-pressure test. It includes volume sensing apparatus 38 and an indicator represented by the block 40 labelled VOLUME MEASUREMENT. The representation is schematic. The apparatus need be nothing more than what has been used in the past to conduct the Department of Transportation's hydrostatic tests.

A vessel 42 is held suspended in the body of water 44 with which the jacket is filled. The jacket is covered and completely filled and sealed with a cover 46 to permit accurate measurement of the vessel's volumetric change in the hydrostatic pressure test. In this embodiment the vessel is suspended from the cover. The suspension apparatus 48 includes a coupling 50 which permits rotation of the vessel 42 and through which the vessel may be pressurized by a pump 52 through a conduit 54.

Thus, in this case there are eight acoustic event sensor and preamplifier units fixed to the vessel itself according to a pre-established pattern. In this case all eight are uniformly spaced approximately four feet and eight inches apart along a single vertical line. Their function is to provide electrical signals whose wave shape and amplitude indicate the character of, and the distance to the situs of, acoustic events occurring in the vessel. They permit distinguishing crack growth from noise and the permit locating the situs of the event along the length of the vessel. In the case of a vessel whose outer diameter is less than ten inches, lengthwise location is enough. If further magnetic or sonic testing is indicated, those tests can locate the flaw exactly when the vessel is removed from the test jacket. In the case of another standard vessel size in which a thirty-four foot long vessel is twenty-two inches in diameter, it is useful to expand the test apparatus to permit mapping the point on the circumference at which an event occurred. That requires a different pattern of sensor position or it can be done by adding echo signaling. The latter is employed in this embodiment. The piezoelectric effect is reversible. Subjected to mechanical pressure by sound waves, the piezoelectric element generates an electrical signal. Subjected to varying electrical signals it generates sound waves. After the lengthwise position of an acoustic event is determined. The sensors above and below are made to emit ultrasound signals. Then acting as sensors they record the echo from the fault at which the acoustic event was initiated. The reflection signal being relatively strong, it is possible to use relative time and amplitude information to determine how far around the circumference it is to the flaw. A second echo test after rotating the vessel less than a quarter turn will yield data by which to determine which side of the vessel is flawed.

Especially in the case of small pressure tanks and tanks that have irregular shape, and particularly when no flaw is suspected, it is often convenient to fix a set of sensors directly to the wall of the vessel to be tested. To illustrate that, three such sensors numbered 64, 66 and 68, respectively, are shown to be fixed two to one side and one to the other side of vessel 42. The cable 70 contains the conductors by which all of the sensors are connected to the signal processor.

In obedience to the rules, the best mode now known for practicing the invention has been shown in the accompanying drawing and described in the specification above. However, it is to be understood that other embodiments and variations of the invention are possible and that the invention is to be limited by what is defined in the appended claims rather than by what has been shown.

I claim:
1. In combination:
   (a) a container for water;
   (b) means for immersing a pressure vessel in water in said container;
   (c) pressurization means for altering pressure in the vessel and maintaining the pressure at selected pressures;
   (d) sensor means in the form of at least one acoustic event sensor for sensing acoustic events emanating from flaws which do not extend through the wall of the pressure vessel at predetermined positions relative to the surfaces of said vessel; and
   (e) recording means for recording the characteristics of acoustic events sensed by said sensors.

2. The invention defined in claim 1 including at least two acoustic event sensors arranged to be fixed to the surface of the vessel during the course of a test.

3. The invention defined in claim 1 which comprises a plurality of acoustic event sensors fixed to spaced points on said container for water.

4. In combination:
   (a) a container for water;
   (b) means for immersing a pressure vessel in water in said container;
   (c) pressurization means for altering pressure in the vessel and maintaining the pressure at selected pressures;
   (d) sensor means in the form of at least one acoustic event sensor for sensing acoustic events at predetermined positions relative to the surfaces of said vessel;
   (e) recording means for recording the characteristics of acoustic events sensed by said sensors; and
   (f) said pressurization means being capable of elevating internal vessel pressure in a cycle that includes elevation to a selected pressure less than test pressure, maintaining that pressure for a given period followed by an elevation to pressure to test value and a maintaining of that pressure for a selected time, and thereafter alternately decreasing internal pressure to a value near ambient pressure.

5. The invention defined in claim 4 which further comprises means for measuring any change in volume of a vessel while said vessel is subjected to an increased pressure.

6. In combination:
(a) a container for water;
(b) means for immersing a pressure vessel in water in said container;
(c) pressurization means for altering pressure in the vessel and maintaining the pressure at selected pressures;
(d) sensor means in the form of at least one acoustic event sensor for sensing acoustic events at predetermined positions relative to the surfaces of said vessel;
(e) recording means for recording the characteristics of acoustic events sensed by said sensors;
(f) at least some of said acoustic event sensors being fixed to spaced points on said container for water; and
(g) in which others of said sensors are arranged to be fixed at spaced points to a vessel immersed in water in said container for water.

7. The invention defined in claim 6 which further comprises means for rotating a test container about its vertical axis while suspended in water in said container for water.

8. In combination:
(a) a container for water;
(b) means for immersing a pressure vessel in water in said container;
(c) pressurization means for altering pressure in the vessel and maintaining the pressure at selected pressures;
(d) sensor means in the form of at least one acoustic event sensor for sensing acoustic events at predetermined positions relative to the surfaces of said vessel;
(e) recording means for recording the characteristics of acoustic events sensed by said sensors; and
(f) said pressurization means comprising means for increasing and decreasing pressurization of a vessel over several cycles of increased and decreased pressure while the vessel remains submerged in said container for water.

9. In combination:
(a) a container for water;
(b) means for immersing a pressure vessel in water in said container;
(c) pressurization means for altering pressure in the vessel and maintaining the pressure at selected pressures;
(d) sensor means in the form of at least one acoustic event sensor for sensing acoustic events at predetermined positions relative to the surfaces of said vessel;
(e) recording means for recording the characteristics of acoustic events sensed by said sensors; and
(f) further comprising means for transmitting sonic energy through said water to impinge on said pressure vessel and means for receiving and providing information about the time of arrival and the relative amplitude of any echo of said sonic energy at spaced points in said water.

10. The method of collecting acoustic event data for use in evaluating the structural integrity of pressure vessels, which method comprises the steps of:
(a) immersing a vessel in water;
(b) increasing the internal pressure of the vessel to a selected test pressure above the service pressure of the vessel while it is submerged; and
(c) while maintaining the internal pressure of the vessel at said test pressure, detecting and recording acoustic events resulting from crack growth in the walls of the test vessel.

11. The invention defined in claim 10 in which the step of detecting and recording acoustic events is conducted by detecting such events at spaced points on the outer surface of the vessel.

12. The invention defined in claim 10 in which the step of detecting and recording acoustic events is conducted while said vessel is filled with water.

13. The invention defined in claim 12 in which the step of detecting and recording acoustic events is accomplished by detecting said events at points spaced from one another and from said vessel.

14. The invention defined in claim 12 which comprises the further step of mapping the approximate position of the origin of any acoustic events as a function of at least one of the time of arrival or the amplitude of such acoustic events.

15. The invention defined in claim 10 in which the volumetric increase in said vessel incident so such pressurization is measured.

16. The method of collecting acoustic event data for use in evaluating the structural integrity of pressure vessels, which method comprises the steps of:
(a) immersing a vessel in water;
(b) increasing the internal pressure of the vessel to a selected test pressure above the service pressure of the vessel while it is submerged; and
(c) while maintaining the internal pressure of the vessel at said test pressure, detecting and recording acoustic events in the walls of the test vessel;
(d) the step of detecting and recording acoustic events being conducted while said vessel is filled with water; and
(e) the step of detecting and recording acoustic events being conducted by detecting said events both at spaced points on the surface of the vessel and at points exposed to the water in which the vessel is immersed and which are spaced from one another and from said vessel.

17. The method of collecting acoustic event data for use in evaluating the structural integrity of pressure vessels, which method comprises the steps of:
(a) immersing a vessel in water;
(b) increasing the internal pressure of the vessel to a selected test pressure above the service pressure of the vessel while it is submerged; and
(c) while maintaining the internal pressure of the vessel at said test pressure, detecting and recording acoustic events in the walls of the test vessel; and
(d) the steps of increasing the pressure within the vessel and of detecting and recording acoustic events being repeated in a series of tests separated by periods of pressure reduction to not more than service pressure.

18. The invention defined in claim 17 in which the first test in said series of tests is conducted while the vessel is pressurized to a value higher than the pressure to which it is pressurized in the remaining tests of said series of tests.

19. The method of collecting acoustic event data for use in evaluating the structural integrity of pressure vessels, which method comprises the steps of:

(a) immersing a vessel in water;
(b) increasing the internal pressure of the vessel to a selected test pressure above the service pressure of the vessel while it is submerged; and
(c) while maintaining the internal pressure of the vessel at said test pressure, detecting and recording acoustic events in the walls of the test vessel;
(d) the step of detecting and recording acoustic events being conducted while said vessel is filled with water;
(e) the further step of transmitting sonic energy through the water in which said vessel is immersed and receiving echoes of said energy at spaced points in said water; and
(f) utilizing at least one of the difference in amplitude if energy in an echo at said points or the difference in arrival time of the echo at said spaced points to find the probable point from which the echo was reflected.

* * * * *